United States Patent [19]
Clark et al.

[11] Patent Number: 5,126,324
[45] Date of Patent: Jun. 30, 1992

[54] METHOD OF ENHANCING GROWTH IN PATIENTS USING COMBINATION THERAPY

[75] Inventors: Ross G. Clark, Pacifica; Michael J. Cronin, San Mateo, both of Calif.

[73] Assignee: Genentech, Inc., South San Francisco, Calif.

[21] Appl. No.: 535,005

[22] Filed: Jun. 7, 1990

[51] Int. Cl.$^5$ .............................................. A61K 37/36
[52] U.S. Cl. ........................................ 514/12; 514/3; 514/4; 514/21
[58] Field of Search ........................... 514/4, 3, 12, 21

[56] References Cited

FOREIGN PATENT DOCUMENTS

WO89/09792 10/1989 PCT Int'l Appl. .

OTHER PUBLICATIONS

*The Merck Index*, 9th ed., Merck & Co. Inc., Rahway, N.J. 1976, p. 7361, entry No. 7360.
Baxter & Martin, Progr. in Growth Factor Res., 1:49–68 (1989).
Roghani et al., FEBS Ltrs., 255(2):253–258 (1989).
Bautista et al., Clin. Res., 38(1):117A (1990).
Ballard et al., Acta Endocr., 121:751–752 (1989).
Lee et al., Mol. Endocr., 2(5):404–411 (1988).
Binkert et al., EMBO J., 8(9):2497–2502 (1989).
Rosenfeld et al., J. Clin. Endocr. & Metab., 70(2):551–553(1990).
Mohan et al., PNAS USA, 86:8338–8342 (1989).
Shimonaka et al., BBRC, 165(1):189–195 (1989).
Pell & Bates, Workshop on Current Trends in Growth Related Research, Haifa, Israel, Oct. 24–27, 1989 (43).
Guler et al., Acta Endocr., 121:456–464 (1989).
Froesch et al., Trends in Endocr. & Metab., 1(5):254–260 (1990).
Moore et al., Endocrin., 122(6):2920–2926 (1988).
Salmon & Daughaday, J. Lab & Clin. Med., 49(6):825–836 (1957).
Guler et al., PNAS, USA, 85:4889–4893 (1988).
Isgaard et al., Am. J. Physiol., 250:E367–E372 (1986).
Ernst & Froesch, BBRC, 151(1):142–147 (1988).
Lobie et al., Endocrin., 126(1):299–306 (1990).
Robinson & Clark, Acta Poediatr Scand (Suppl), 347:93–103 (1988).
Merchau et al., J. Clin. Invest., 81:791–797 (1988).
Schwartz et al., PNAS, USA, 82:8724–8728 (1985).
Lindahl et al., Endocrin., 121(3):1070–1075 (1987).
Cook et al., J. Clin. Invest., 81:206–212 (1988).
Isgaard et al., Endocrin., 123(6):2605–2610 (1988).
Nilsson et al., Calc. Tiss. Int., 40:91–96 (1987).
Otonkoski et al., Diabetes, 37:1678–1683 (1988).
Tippel et al., Pediatric Res., 25(1):76–82 (1989).
Yamashita et al., J. Biol. Chem., 262(27):13254–13257 (1987).
Van Neste et al., J. Endocr., 119:69–74 (1988).
Rosselot et al., The Endocrine Soc. 72$^{nd}$ Ann. Mtg, Abst., 202 p. 75 (Jun. 1990).
Skottner et al., J. Endocrin., 112:123–132 (1987).
Horikawa et al., Eur. J. Pharmacol., 166:87–94 (1989).
Skottner et al., Endocrin., 124(5):2519–2526 (1989).
Schoenle et al., Acta Endocrinologica, 108:167–174 (1985).
Namba et al., Endocrin., 124(4):1794–1799 (1989).
Young et al., J. Endocrin., 121:563–570 (1989).

(List continued on next page.)

Primary Examiner—F. T. Moezie
Attorney, Agent, or Firm—Janet E. Hasak

[57] ABSTRACT

A method is disclosed for enhancing growth of a mammal by administration of a combination of effective amounts of IGF-I and GH so as to enhance the growth of the mammal over the enhancement in growth achieved using either IGF-I or GH alone in an amount equal to that used for either IGF-I or GH, respectively, in the combination. Preferably, the mammal is a child, the IGF-I is native-sequence, mature human IGF-I or human brain IGF-I, and the GH is native-sequence, mature human GH with or without a terminal methionine. In another preferred embodiment, the mammal is a non-human animal of economic importance such as a cow or pig.

29 Claims, 9 Drawing Sheets

OTHER PUBLICATIONS

Smith et al., J. Orthop. Res., 7:198–207 (1989).
Watanabe et al., J. Endocr., 107:275–283 (1985).
Vetter et al., J. Clin. Invest., 77:1903–1908 (1986).
Schlechter et al., Am. J. Physiol., 250:E231–E235 (1986).
Russell & Spencer, Endocrin., 116(6):2563–2567 (1985).
Orlowski & Chernausek, Endocrin., 123(1):44–49 (1988).
Philips & Vassilopaolou-Sellin, New Engl. J. Med., 302(7):371–380; 438–446 (1980).
Schlechter et al., PNAS, USA, 83:7932–7934 (1986).
Scheiwiller et al., Nature, 323:169–171 (1986).
Phillips & Vassilopoolou-Sellin, New Engl. J. Med., 302(7): 371–380; 438–446 (1980).
Schlechter et al., PNAS, USA, 83: 7932–7934 (1986).
Scheiwiller et al., Nature, 323: 169–171 (1986).
Zezulak & Green, Science, 233: 551–553 (1986).
Madsen et al., Nature, 304: 545–547 (1983).
Tanner et al., Acta, Endocrinologica, 84: 681–696 (1977).
Isaksson et al., Science, 216: 1237–1239 (1982).
Green et al., Differentiation, 29: 195–198 (1985).
Pell & Bates, J. Endocrin., 123 Suppl. #119 (1989).

```
           7.6  8.9      6.6  7.9      6.8  9.4      4.9  6.8      7.2  8.2
9.0 +
cm/yr 6.0 +
3.0 +
     ----+----------+----------+----------+----------+----------+----------
Prev Rx   Yes  No     Yes  No     Yes  No     Yes  No     Yes  No
Etiology  Idiopathic   Organic     S-O D       Turner      Other
N         664  1035   226  265    57   31     16   249    135  919
Dose      0.071 0.086 0.071 0.080 0.072 0.080 0.083 0.100 0.081 0.091
```

FIG. 8A

METHOD OF ENHANCING GROWTH IN PATIENTS USING COMBINATION THERAPY

BACKGROUND OF THE INVENTION

1. Field of the Invention

This invention relates to a method of enhancing growth in patients, particularly those exhibiting a retarded growth rate or weight loss using a combination of natural hormones. In addition, the combination reduces the degree of imbalance of glucose homeostasis induced by either hormone administered alone.

2. Description of Related Art

Insulin-like growth factor I (IGF-I) is a polypeptide naturally occurring in human body fluids, for example, blood and human cerebral spinal fluid. Most tissues and especially the liver produce IGF-I together with specific IGF-binding proteins. These molecules are under the control of growth hormone (GH). Like GH, IGF-I is a potent anabolic protein. See Tanner et al., *Acta Endocrinol.*, 84: 681-696 (1977); Uthne et al., *J. Clin. Endocrinol. Metab.*, 39: 548-554 (1974)). IGF-I has been isolated from human serum and produced recombinantly See, e.g., EP 123,228 and 128,733.

Various biological activities of IGF-I have been identified. Researchers have found that an intravenous bolus injection of IGF-I lowers blood glucose levels in humans. See Guler et al., *N. Engl. J. Med.*, 317: 137-140 (1987). Additionally, IGF-I promotes growth in several metabolic conditions characterized by low IGF-I levels, such as hypophysectomized rats [Guler et al., *Endocrinology*, 118: Supp 129 abstract, Skottner et al., *J. Endocr.*, 112: 123-132 (1987); Guler et al., *Proc. Natl. Acad. Sci. USA*, 85: 4889-4893 (1988); Froesch et al., in *Endocrinology, Intl. Congress Series* 655, ed. by Labrie and Proulx (Amsterdam: Excerpta Medica, 1984), p. 475-479], diabetic rats [Scheiwiller et al., *Nature*, 323: 169-171 (1986)], and dwarf rats [Skottner et al., *Endocrinology*, 124: 2519-2526 (1989)]. The kidney weight of hypophysectomized rats increases substantially upon prolonged infusions of IGF-I subcutaneously. Guler et al., *Proceedings of the 1st European Congress of Endocrinology*, 103: abstract 12-390 (Copenhagen, 1987). The kidneys of Snell dwarf mice and dwarf rats behaved similarly. van Buul-Offers et al., *Pediatr. Res.*, 20: 825-827 (1986); Skottner et al., *Endocrinology*, supra. An additional use for IGF-I is its administration to improve glomerular filtration and renal plasma flow in human patients. See EP 327,503 published Aug. 9, 1989; Guler et al., *Proc. Natl. Acad. Sci. USA*, 86: 2868-2872 (1989).

Human growth hormone (hGH) is a single-chain polypeptide consisting of 191 amino acids (molecular weight 2,500). Disulfide bonds link positions 53 and 165 and positions 182 and 189. Niall, *Nature, New Biology*, 230: 90 (1971). Human GH is a potent anabolic agent, especially due to retention of nitrogen, phosphorus, potassium, and calcium. Treatment of hypophysectomized rats with GH can restore at least a portion of the growth rate of an intact animal Moore et al., *Endocrinology*, 122: 2920-2926 (1988). Among its most striking effects in hypopituitary (GH-deficient) subjects is accelerated linear growth of bone growth plate cartilage resulting in increased stature. Kaplan, *Growth Disorders in Children and Adolescents* (Springfield, IL: Charles C. Thomas, 1964).

In 1957, the mechanism of GH action was postulated as being due to GH inducing production of somatomedins (subsequently identified and named IGF-I) in the liver, which travel via the circulation to produce all the effects of GH. Salmon and Daughaday, *J. Lab. Clin. Med.*, 49: 825-836 (1957). Many studies investigating the relationships among GH, IGF-I, cartilage, cultured human fibroblasts, skeletal muscle, and growth have supported this somatomedin hypothesis. See, e.g., Phillips and Vassilopoulou-Sellin, *N. Enol. J. Med.*, 302: 372-380; 438-446 (1980); Vetter et al., *J. Clin. Invest.*, 7: 1903-1908 (1986); Cook et al., *J. Clin. Invest.*, 81: 206-212 (1988); Isgaard et al., *Endocrinology*, 123: 2605-2610 (1988); Schoenle et al., *Acta Endocrin.*, 108: 167-174 (1985).

Another theory holds that GH has a direct effect on chondrocytes that is not dependent on circulating IGF-I. For example, several in vivo studies have demonstrated longitudinal long bone growth in rats receiving hGH injected directly into the tibial growth plate [Isaksson et al., *Science*, 216: 1237-1239 (1982); Russell and Spencer, *Endocrinology*, 116: 2563-2567 (1985)] or the arterial supply to a limb [Schlechter et al., *Am. J. Physiol.*, 250: E231-235 (1986)]. Additionally it was found that proliferation of cultured lapine ear and rib chondrocytes in culture is stimulated by hGH [Madsen et al., *Nature*, 304: 545-547 (1983)], this being consistent with a direct GH effect or with an indirect effect of GH mediated by local GH-dependent IGF-I production. Such an autocrine or paracrine model for stimulation of growth has been supported by various lines of experimental evidence. Schlechter et al., *Proc. Natl. Acad. Sci. USA.* 83: 7932-7934 (1986); Nilsson et al., *Calcif. Tissue Int.*, 40: 91-96 (1987). Nilsson et al. showed that while unilateral arterial infusion of IGF-I did not produce a tibial longitudinal bone growth response in hypophysectomized rats, infusion of hGH did induce such growth. Moreover, the influence of GH on the functional maturation of human fetal islet cells in vitro could not be reproduced by adding IGF-I, suggesting a direct rather than a somatomedin-mediated action of GH for these particular cells. Otonkoski et al., *Diabetes.* 37: 1678-1683 (1988).

A third theory for GH and IGF-I actions is that GH promotes differentiation of stem cells, rendering them responsive to stimulation of proliferation by IGF-I. Green et al., *Differentiation*, 29: 195-198 (1985). Although support for this model of GH acting to produce IGF-I locally, called the dual effector theory, has been obtained for certain cell types [Zezulak and Green, *Science*. 233: 551-553 (1986)], its application to skeletal growth has not been established. It has been found that both GH and testosterone could stimulate skeletal growth in the hypophysectomized prepubertal lamb without alteration of circulating IGF-I concentrations, the results not precluding the possibility that the growth-promoting effect of GH was affected by local actions at the site of osteogenesis. Young et al., *J. Endocrin.*, 121: 563-570 (1989). Also, GH has been reported to stimulate tibial epiphyseal plate width in the hypophysectomized rat without increasing circulating IGF-I concentrations. Orlowski and Chernausek, *Endocrinol.*, 123: 44-49 (1988).

More recently, a study was undertaken to reproduce the "direct" in vitro GH effect on epiphyseal and articular chondrocytes to determine whether this effect is mediated by IGF-I in a local autocrine or paracrine fashion. Trippel et al., *Pediatr. Res.*, 25: 76-82 (1989). Human GH was found not to stimulate rabbit articular or epiphyseal chondrocytes or bovine epiphyseal chondrocytes, whereas IGF-I stimulated both mitotic and differentiated cell functions in both epiphyseal and articular chondrocytes. The authors state that the data suggest that the role of IGF-I in skeletal development is complex and may be diverse both in the cellular functions it regulates and the cell populations regulated, requiring further investigation to define the relationship of IGF-I to GH.

It has been reported that the growth response to co-addition of GH and IGF-I was not statistically different from that of GH alone when body weight gain, bone length, or tibial epiphyseal cartilage width was measured. Skottner et al., *J. Endocr.*, supra [*iv infusion of bGH* (10 mu/day) for 8 days and met-IGF-I (with specific activity of 3400 U/mg, 120 µg/day) for the last 4 days]; Isgaard et al., *Am. J. Physiol.*, 250: E367-E372 (1986) [5 µg of IGF-I and 1 µg of hGH injected locally daily for 5 days]. It was also found that IGF-I, when injected or infused subcutaneously or infused intravenously, is a weak growth promoter in hypophysectomized rats compared with hGH, even when infused in combination with small amounts of hGH. Robinson and Clark, *Acta Paediatr. Scand. Supp.* 347: 93-103 (1988).

As regards osteoblast-like cells in culture, direct stimulation of their proliferation by hGH is at least partially mediated by IGF-I-like immunoreactivity [Ernst and Froesch, *Biochem Biophy Res. Commun.*, 151: 142-147 (1988)]; the authors found that IGF-I and hGH had additive effects on osteoblast proliferation only when the exogenous IGF-I concentration exceeded that of endogenously produced IGF-I by a large margin. Another in vitro study showed that purified human and synthetic IGF-I stimulated adult articular chondrocyte DNA and proteoglycan synthesis; GH had no effect on either process; and GH added in combination with IGF-I increased proteoglycan, cell-associated proteoglycan, and keratan sulfate synthesis over levels observed with IGF-I alone. Smith et al., *J. Orthop. Res.*, 7: 198-207 (1989). Separate administration of hGH and IGF-I was found to enhance human granulopoiesis, with the effect of hGH on marrow myeloid progenitors apparently mediated by paracrine IGF-I. Merchav et al., *J. Clin. Invest.*, 81: 791-797 (1988). Merchav et al. also noted that myeloid colony formation was significantly enhanced in cultures stimulated with combined limiting concentrations of both IGF-I and hGH, whereas combined maximal concentrations of both peptides did not exert an additive effect.

Also, based on recent immunohistochemical data regarding the GH receptor, it has been suggested that GH may act independently of or synergistically with hepatic IGF-I in carrying out its growth-promoting role in the gastrointestinal tract. Lobie et al., *Endocrinol.*, 126: 299-306 (1990). It has been shown that pretreatment of hypophysectomized rats with GH, but not with IGF-I, promotes the formation of chondrocyte colonies and makes the chondrocytes susceptible to IGF-I in vitro. Lindahl et al., *Endocrinol.*, 121: 1070-1075 (1987). The authors suggest that GH induces colony formation by IGF-I-independent mechanisms and that IGF-I is a second effector in GH action. Further, treatment of hypophysectomized animals with a single dose of hGH restored IGF-I mRNA in parenchymal and in non-parenchymal cells to the extent found in intact animals. van Neste et al., *J. Endocr.*, 119: 69-74 (1988).

However, it has also been reported that IGF-I directly suppresses GH gene transcription and GH secretion at the pituitary level in an inhibitory feedback control mechanism. Namba et al., *Endocrinol.*, 124: 1794-1799 (1989); Yamashita et al., J. Biol. Chem., 262: 13254-3257 (1987). Additionally, it was reported that the maximum stimulation of glucose metabolism in 3T3 adipocytes achieved by hGH is only a fraction of that produced by various IGFs, indicating that extracellular IGFs do not mimic the effects of hGH on glucose metabolism in these adipocytes. Schwartz et al., *Proc. Natl. Acad. Sci. USA*, 82: 8724-8728 (1985). Moreover, human GH was found not to enhance further the IGF-I-stimulated Leydig cell steroidogenesis. Horikawa et al., *Eur. J. Pharmacol.*, 166: 87-94 (1989). Another negative finding was that the combination of chick growth hormone and human IGF-I did not stimulate cell proliferation and metabolic activity of cultured epiphyseal growth plate chondrocytes above human IGF-I alone. Rosselot et al., *The Endocrine Society* 72nd Annual Meeting, abstract 202, p. 75, of Program and Abstracts released prior to the meeting in Atlanta, GA on June 20-23, 1990. It has also been reported that both hGH and hIGF-I can promote growth in the mutant dwarf rat, but they differ both quantitatively and qualitatively in their pattern of actions. Skottner et al., *Endocrinology*, supra. Additionally, a loss of IGF-I receptors in cultured bovine articular chondrocytes was found after pre-exposure of the cells to pharmacological doses of either hGH or bGH. Watanabe et al., *J. Endocr.*, 107: 275-283 (1985). The necessity for large amounts of GH is attributed to extremely low affinity of GH binding sites on these cells. The authors speculate that living organisms have a protection mechanism to avoid unnecessary overgrowth of the body resulting in down-regulation of the IGF-I receptors.

U.S. Pat. No. 4,857,505 issued Aug. 15, 1989 discloses use of an adduct of a growth hormone, growth factor, IGF-I, or fragment thereof covalently bonded to an activated polysaccharide for increased half-life, increased weight gain in animals, and increased milk production.

Known side effects of hGH treatment include sodium retention and expansion of extracellular volume [Ikkos et al., *Acta Endocrinol.* (Copenhagen), 32: 341-361 (1959); Biglieri et al., *J. Clin. Endocrinol. Metab.*, 21: 361-370 (1961)], as well as hyperinsulinemia and hyperglycemia. The major apparent side effect of IGF-I is hypoglycemia. Guler et al., *Proc. Natl. Acad. Sci. USA*, 1989, supra.

It is an object of the present invention to provide a combination of IGF-I and GH that has a greater effect on growth of patients than either hormone alone.

It is another object to provide a method for treating patients, whether children or adults, that experience a reduced anabolic effect of GH, as by a reduced ability to produce an IGF-I response to the GH, or experience diabetogenic effects or other side effects when treated with GH alone, or hypoglycemia when treated with IGF-I alone.

These and other objects will be apparent to those of ordinary skill in the art.

SUMMARY OF THE INVENTION

Accordingly, the present invention provides a method for enhancing growth of a mammal comprising administering to the mammal effective amounts of IGF-I and GH so as to enhance the growth of the mammal over the enhancement in growth achieved using the same amount of IGF-I or GH singly as is used for IGF-I or GH, respectively, in combination.

In another aspect, the invention provides a cell-free growth-promoting composition comprising amounts of IGF-I and GH in a pharmaceutically acceptable carrier that are effective to promote growth of a mammal more than the promotion of growth achieved using the same amount of IGF-I or GH singly as is used for IGF-I or GH, respectively, in combination.

In still another aspect, the invention provides a growth-promoting composition comprising IGF-I and GH in a pharmaceutically acceptable carrier at about pH 6 containing a surfactant.

The literature shows that the role of IGF-I in skeletal development in conjunction with GH is complex, and evidence supporting various theories of GH action is contradictory and inconclusive. If GH acts via production of circulating IGF-I (the somatomedin hypothesis), then a maximal dose of GH would not be expected to be enhanced by administering IGF-I systemically. If GH acts locally to produce IGF-I, then it is unlikely that the high local concentrations of IGF-I predicted by this second theory could be reproduced by administering IGF-I systemically. If some actions of GH do not involve IGF-I generation, then adding GH might enhance the effect of IGF-I. However, in view of the confusion surrounding which of these three unresolved theories is correct, there was no clear basis to predict the outcome on body and bone growth of administering to a mammal a combination of GH and IGF-I.

Unexpectedly, a significantly greater daily body weight gain, increased longitudinal bone growth, and enhanced epiphyseal width of the tibia were achieved after combination treatment with IGF-I and GH as compared with the same doses of each of IGF-I and GH alone. Further, the additive effect of IGF-I and GH was not seen for all tissues, indicating a selectivity for whole body growth, bone, and cartilage. Moreover, IGF-I enhanced the growth-promoting effect of GH even at the maximum effective dose of GH, and can further enhance a low dose of GH to produce a maximal growth response. Thus, IGF-I may be used in combination with lower doses of GH to increase growth of those immature patients that have reached their maximum growth rate after treatment with maximal doses of GH alone and then experienced a fall in their annualized growth rate. This is an effect that is widespread in all growth-deficient patients after several months of treatment. The combination could also be used to maximize the growth response in patients who present late in development with growth retardation, and only have a few years of therapeutic intervention potential. Additionally, the combination can be used to treat those patients who exhibit side effects such as diabetogenic symptoms with maximum doses of GH or hypoglycemia with maximum doses of IGF-I.

BRIEF DESCRIPTION OF THE DRAWINGS

FIG. 8 illustrates bar graphs of the growth rate in cm/year of patients of various growth inhibition etiologies having had either no previous treatment (Prev Rx No) or previous treatment (Prev Rx Yes) with hGH. N indicates the number of patients at the indicated dose level of hGH given in units of mg/kg. FIG. 8A is the data for the first year of hGH treatment and FIG. 8B is for the second year of hGH treatment.

DESCRIPTION OF THE PREFERRED EMBODIMENTS

A. Definitions

Figure 1A:
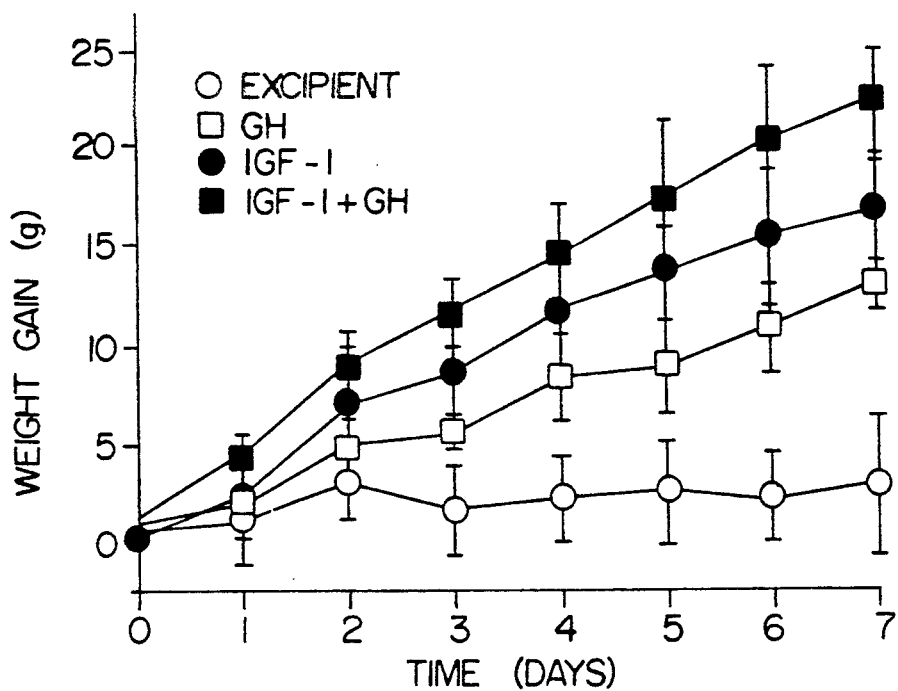
FIGS. 1A and 1B represent graphs of cumulative body weight gain over seven days for each group of treated hypophysectomized adult male rats for two replicate studies 1 and 2, respectively, performed one month apart (means±SD).

As used herein, "mammal" signifies humans as well as animals, and includes animals of economic importance such as bovine, ovine, and porcine animals. The preferred mammal herein is a human. The term "non-adult" refers to mammals that are from perinatal age (such as low-birth-weight infants) up to the age of puberty, the latter being those that have not yet reached full growth potential.

As used herein, "IGF-I" refers to insulin-like growth factor from any species, including bovine, ovine, porcine, equine, and preferably human, in native-sequence or in variant form, and from any source, whether natural, synthetic, or recombinant. Preferred herein for animal use is that form of IGF-I from the particular species being treated, such as porcine IGF-I to treat pigs, ovine IGF-I to treat sheep, bovine IGF-I to treat cattle, etc. Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, CA for clinical investigations. Also preferred for use is IGF-I that has a specific activity greater than about 14,000 units/mg as determined by radioreceptor assay using placenta membranes, such as that available from KabiGen AB, Stockholm, Sweden.

The most preferred IGF-I variants are those described in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1-3)-IGF-I, or des-IGF-I).

As used herein, "GH" refers to growth hormone from any species, including bovine, ovine, porcine, equine, and preferably human, in native-sequence or in variant form, and from any source, whether natural, synthetic, or recombinant. Preferred herein for animal use is that form of GH from the particular species being treated, such as porcine GH to treat pigs, ovine GH to treat sheep, bovine GH to treat cattle, etc. Preferred herein for human use is human native-sequence, mature GH with or without a methionine at its N-terminus. Also preferred is recombinant hGH, i.e., that produced by means of recombinant DNA technology. More preferred is methionyl human growth hormone (met-hGH) produced in *E. coli*, e.g., by the process described in U.S. Pat. No. 4,755,465 issued Jul. 5, 1988 and Goeddel et al., *Nature*, 282: 544 (1979). Met-hGH, which is sold under the trademark PROTROPIN ® by Genentech, Inc., is identical to the natural polypeptide, with the exception of the presence of an N-terminal methionine residue. This added amino acid is a result of the bacterial protein synthesis process.

Another preferred hGH for human use is a recombinant hGH (rhGH), available to clinical and research investigators from Genentech, Inc. under the trademark NUTROTIN ®, and commercially available from Eli Lilly, that lacks this methionine residue and has an amino acid sequence identical to that of the natural hormone. See Gray et al., *Biotechnology*, 2: 161 (1984). Both met-hGH and rhGH have equivalent potencies and pharmacokinetic values. Moore et al., supra.

As used herein, the term "growth" refers to the dynamics of statural growth experienced by an individual during infancy, childhood, and adolescence as depicted by a normal growth curve. Thus, growth herein refers to the growth of linear-producing bone plate driven by chondrocytes, as distinguished from the growth of osteoblast cells, derived from a different part of the bone. Restoration of normal growth patterns would allow the patient to approach a more satisfactory growth curve. Examples of patients that are relatively resistant to GH but require treatment to induce an anabolic effect include those with Turner's Syndrome, GH-deficient children who grow poorly in response to GH treatment, children who experience a slowing or retardation in their normal growth curve about 2-3 years before their growth plate closes, so that GH administered alone would no longer increase growth of the children, so-called short normal children, and patients where the IGF-I response to GH has been blocked chemically (i.e., by glucocorticoid treatment) or by a natural condition such as in adult patients where the IGF-I response to GH is naturally reduced.

B. Modes for Carrying Out the Invention

The IGF-I and GH are directly administered to the mammal by any suitable technique, including parenterally, intranasally, or orally. They need not be administered by the same route and can be administered locally or systemically. The specific route of administration will depend, e.g., on the medical history of the patient, including any perceived or anticipated side or reduced anabolic effects using hGH or IGF-I alone, and the growth defect to be corrected. Examples of parenteral administration include subcutaneous, intramuscular, intravenous, intraarterial, and intraperitoneal administration. Most preferably, the administration is by continuous infusion (using, e.g., minipumps such as osmotic pumps), or by injection (using, e.g., intravenous or subcutaneous means). Preferably, the administration is subcutaneous for both IGF-I and GH. The administration may also be as a single bolus or by slow-release depot formulation. Most preferably, the IGF-I is administered continuously by infusion, most preferably subcutaneously, and the GH is administered daily subcutaneously by injection.

In addition, the IGF-I is suitably administered together with its binding protein, for example, BP53, which is described in WO 89/09268 published Oct. 5, 1989 and by Martin and Baxter, *J. Biol. Chem.* 261: 8754-8760 (1986), the disclosures of which are incorporated herein by reference. This protein is an acid-stable component of about 53 Kd on a non-reducing SDS-PAGE gel of a 125-150 Kd glycoprotein complex found in human plasma that carries most of the endogenous IGFs and is also regulated by GH. The IGF-I is also suitably coupled to a receptor or antibody or antibody fragment for administration. Similarly, the GH can be delivered coupled to another agent such as an antibody, an antibody fragment, or one of its binding proteins.

The IGF-I and GH composition(s) to be used in the therapy will be formulated and dosed in a fashion consistent with good medical practice, taking into account the clinical condition of the individual patient (especially the side effects of treatment with hGH or IGF-I alone or growth retardation after continuous GH treatment), the site of delivery of the IGF-I and GH composition(s), the method of administration, the scheduling of administration, and other factors known to practitioners. The "effective amounts" of each component for purposes herein are thus determined by such considerations and must be amounts that enhance growth of the treated patient over growth enhancement that is obtained using the same amount of IGF-I or GH individually.

As a general proposition, the total pharmaceutically effective amount of each of the IGF-I and GH administered parenterally per dose will be in the range of about 1 $\mu$g/kg/day to 100 mg/kg/day of patient body weight, although, as noted above, this will be subject to a great deal of therapeutic discretion. More preferably, this dose is at least 0.1 mg/kg/day, and most preferably at least 1 mg/kg/day for each hormone. If given continuously, the IGF-I and GH are each typically administered at a dose rate of about 1 $\mu$g/kg/hour to about 50 $\mu$g/kg/hour, either by 1-4 injections per day or by continuous subcutaneous infusions, for example, using a minipump. An intravenous bag solution may also be employed. The key factor in selecting an appropriate dose is the result obtained, as measured by increases in body weight gain, lean body mass, or statutory growth approximating the normal range, or by other criteria for measuring growth as defined herein as are deemed appropriate by the practitioner.

The IGF-I and GH are also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (U. Sidman et al., *Biopolymers,* 22,547–556 (1983)), poly(2-hydroxyethyl methacrylate) (R. Langer et al., *J. Biomed. Mater. Res.,* 15: 167–277 (1981), and R. Langer, Chem. Tech., 12: 98–105 (1982)), ethylene vinyl acetate (R. Langer et al., Id.) or poly-D-(-)-3-hydroxybutyric acid (EP 133,988). Sustained-release IGF-I compositions also include liposomally entrapped IGF-I. Liposomes containing IGF-I are prepared by methods known per se: DE 3,218,121; Epstein et al., *Proc. Natl. Acad. Sci.* U.S.A., 82: 3688–3692 (1985); Hwang et al., *Proc. Natl. Acad. Sci.* U.S.A., 77,: 4030–4034 (1980); EP 52,322; EP 36,676; EP 88,046; EP 143,949; EP 142,641; Japanese Pat. Appln. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal IGF-I and GH therapy.

For parenteral administration, in one embodiment, the IGF-I and GH are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I and GH each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine,; monosaccharides, disaccharides, and other carbohydrates including cellulose or its derivatives, glucose, mannose, or dextrins; chelating agents such as EDTA; sugar alcohols such as mannitol or sorbitol; counterions such as sodium, and/or nonionic surfactants such as polysorbates, poloxamers, or PEG.

The IGF-I and GH are each typically formulated individually in such vehicles at a concentration of about 0.1 mg/ml to 100 mg/ml, preferably 1–10 mg/ml, at a pH of about 4.5 to 8. Full-length IGF-I is generally stable at a pH of no more than about 6; des(1-3)-IGF-I is stable at about 3.2 to 5; hGH is stable at a higher pH of, e.g., 7.4–7.8. It will be understood that use of certain of the foregoing excipients, carriers, or stabilizers will result in the formation of IGF-I or GH salts.

In addition, the IGF-I and GH, preferably the full-length IGF-I, are suitably formulated together in a suitable carrier vehicle to form a pharmaceutical composition that does not contain cells. In one embodiment, the buffer used for formulation will depend on whether the composition will be employed immediately upon mixing or stored for later use. If employed immediately after mixing, a mixture of full-length IGF-I and GH can be formulated in mannitol, glycine, and phosphate, pH 7.4. If this mixture is to be stored, it is formulated in a buffer at a pH of about 6, such as citrate, with a surfactant that increases the solubility of the GH at this pH, such as 0.1% polysorbate 20 or poloxamer 188. The final preparation may be a stable liquid or lyophilized solid.

IGF-I and GH to be used for therapeutic administration must be sterile. Sterility is readily accomplished by filtration through sterile filtration membranes (e.g., 0.2 micron membranes).

Therapeutic IGF-I and GH compositions generally are placed into a container having a sterile access port, for example, an intravenous solution bag or vial having a stopper pierceable by a hypodermic injection needle.

IGF-I and GH ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous GH solution, and the resulting mixture is lyophilized. The infusion solution is prepared by reconstituting the lyophilized GH using bacteriostatic Water-for-Injection.

The invention will be more fully understood by reference to the following examples. They should not, however, be construed as limiting the scope of the invention. All literature and patent citations are expressly incorporated by reference.

EXAMPLE I

I. Protocol

Hypophysectomized adult male rats weighing 85 to 105 grams (Taconic, NY) were received 7 days after surgery and then weighed every 2–3 days for ten days to meet entry criteria of a weight gain of less than 7 grams and no overall body weight loss. The rats were maintained on Purina rat chow ad libitum. Each lot of animals was divided into a control (excipient), a IGF-I-supplemented group, a des(1-3)-IGF-I-supplemented group, a GH-supplemented group, a IGF-I/GH-supplemented group, and a des(1-3)-IGF-I/GH-supplemented group.

Alzet osmotic pumps (Alza, Palo Alto, CA) were implanted to deliver continuously either excipient (10 mM citrate buffer and 126 mM NaCl, pH 6.0) or recombinant human IGF-I (produced in *E. coli* as a Z—Z fusion polypeptide by the process generally described in EP 230,869 published Aug. 5, 1987, or available commercially from KabiGen AB, Stockholm, Sweden (specific activity > 14,000 U/mg by radioreceptor assay using placental membranes), or available for clinical investigations from Genentech, Inc., South San Francisco). The IGF-I was dissolved at 5 mg/ml in 10 mM citrate buffer and 126 mM NaCl, pH 6.0 and delivered to the rats at a rate of 120 μg/rat per day (equivalent to 1.2 mg/kg/day assuming that the rats weigh 100 g each). This rate represents a submaximal dose that gives a consistent body weight gain in this model.

Alternatively, the pumps were implanted to deliver continuously recombinant human des(1-3)-IGF-I (produced in $E.\ coli$ as generally described by PCT WO 87/01038 published Feb. 26, 1987 and expected to have a specific activity of >about 14,000 U/mg by radioreceptor assay using placenta membranes, or available as brain IGF from KabiGen AB, Stockholm, Sweden, >14,000 U/mg by radioreceptor assay using placenta membranes). It was then formulated at 2 mg/ml in 20 mM acetic acid, pH 3.2, and delivered at a rate of 0.055, 0.166, or 0.5 mg/kg/day.

To the GH-supplemented groups was delivered recombinant methionyl human growth hormone (Protropin ® brand, Genentech, Inc., South San Francisco, CA) dissolved at 2 mg/ml in 16 mg/ml mannitol and 5 mM phosphate, pH 7.8, as excipient. The hGH was injected subcutaneously each day, also at submaximal doses (15, 60, and 240 μg/kg per day) for the weight gain response. Moore et al., supra.

Alternatively, recombinant (metless) human growth hormone (Nutropin ® brand, Genentech, Inc.) may be employed that is formulated at 2 mg/ml in 18 mg/ml mannitol, 0.68 mg/ml glycine, and 5 mM phosphate, pH 7.4.

At pump implant the animals received oxytetracycline in a single intraperitoneal injection as an intravital marker of longitudinal bone growth.

The growth rates of the hypophysectomized animals were determined by following daily body weights, organ weights at sacrifice, and tibial bone fixed for subsequent assessment of the growth plate. The bone was decalcified, bisected longitudinally, and embedded in paraffin for sectioning and staining with toluidine blue. The distance between the germinal cell layer and the transition from active chondrocytes to new bone deposits was measured microscopically with the aid of a calibrated ocular micrometer. In addition, undecalcified sections were prepared from the proximal tibia and the distance between the growth plate and the tetracycline line, laid down in calcified bone, was determined to assess cumulative longitudinal bone growth.

The remaining solution was removed from all osmotic pumps, and verified by immunoassay to contain either excipient, IGF-I, or des(1-3)-IGF-I. Furthermore, the amount of hormones remaining in the pump of each rat was that expected for continuous delivery over seven days at the rate of delivery specified by the manufacturer.

Independent replicate studies are designated as Study 1 and Study 2, performed a month apart. Statistical comparisons were made by an analysis of variance with follow-up comparisons made by Duncan's Multiple Range Test. A p value of less than 0.05 was considered significant. All data are represented as the mean±SD of 6-8 animals per group. Two other independent studies confirmed these data.

II. Results

Figure 1B:
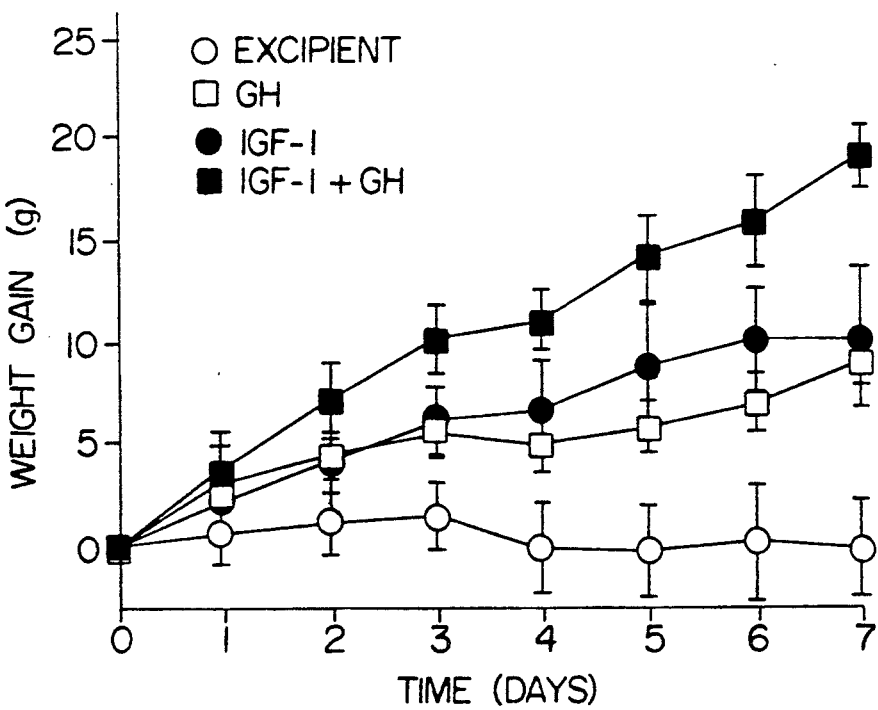

FIGS. 1A and 1B represent the cumulative daily body weight increments for the hypophysectomized rats treated with either excipient, 60 μg/kg/day hGH, 1.2 mg/kg/day IGF-I, or the hGH/IGF-I combination for seven days for Studies 1 and 2, respectively. The mean±SD of 7-9 animals/group is shown in the graphs; statistical significance was assumed if $p<0.05$. The excipient control group did not gain or lose a significant amount of weight during the week, confirming the completeness of the hypophysectomy and the health of the animals in both studies The mean body weight was increased by hGH in a dose-dependent manner such that on days 3-7 the responses to all hGH doses were significantly different from each other (see FIG. 7). Likewise, IGF-I produced a significant body weight gain that was first recognized on day 2 of dosing, and by day 7 was highly significantly different from excipient ($2.9\pm3.5$ g vs. $16.6\pm2.5$ g, $t=16.86$, $p<0.001$).

The combination of hGH plus IGF-I yielded a body weight gain that was greater than either hormone alone and appeared to be at least additive. By day 7, the body weight increments for the excipient control, IGF-I, hGH, and combination treatments were, respectively: Study 1: $2.91\pm3.51$ g, $16.6\pm2.5$ g, $12.9\pm1.2$ g, and $22.2\pm2.7$ g; Study 2: $-0.04\pm2.41$ g, $10.8\pm3$ g, $9.04=0.92$ g, and $19.3\pm1.6$ g. The weight increment of the combination group was statistically different from the means of the other three groups. For example, in Study 1 the mean weight gain at day 7 for the combination ($22.2\pm2.7$ g) was greater than that for GH alone ($12.9\pm1.2$ g, $t=10.80$, $p<0.001$) or for IGF-I alone ($16.6\pm2.5$ g, $t=6.710$, $p<0.001$). In the same experiment (data not shown on this FIG. 1), des-(1-3)-IGF-I also increased weight gain (to $19.9\pm2.6$ g), which on the addition of GH was increased to $24.7\pm1.3$ g ($t=5.75$, $p<0.001$).

In contrast, it was reported earlier that when native bovine GH (bGH) was delivered intravenously for four days to hypophysectomized rats, and then bGH plus methionine-IGF-I for four more days, there was no greater weight gain than that measured with bGH alone. Skottner, $J.\ Endocrin.$, supra. Beyond the different delivery routes and dosing regimens of these two studies, the methionyl-IGF-I itself produced no incremental weight gain in this earlier report. To the contrary, this experiment shows repeatedly that IGF-I and des(1-3)-IGF-I promote body weight gain in hypophysectomized rats and that there was an additive effect when GH was co-delivered.

In the hypophysectomized rat weight gain assay, there is an excellent correlation between the weight gain and the bone growth responses to GH. Therefore, an enhanced weight gain is likely to be accompanied by enhanced bone growth, as is the case below.

Figure 2:
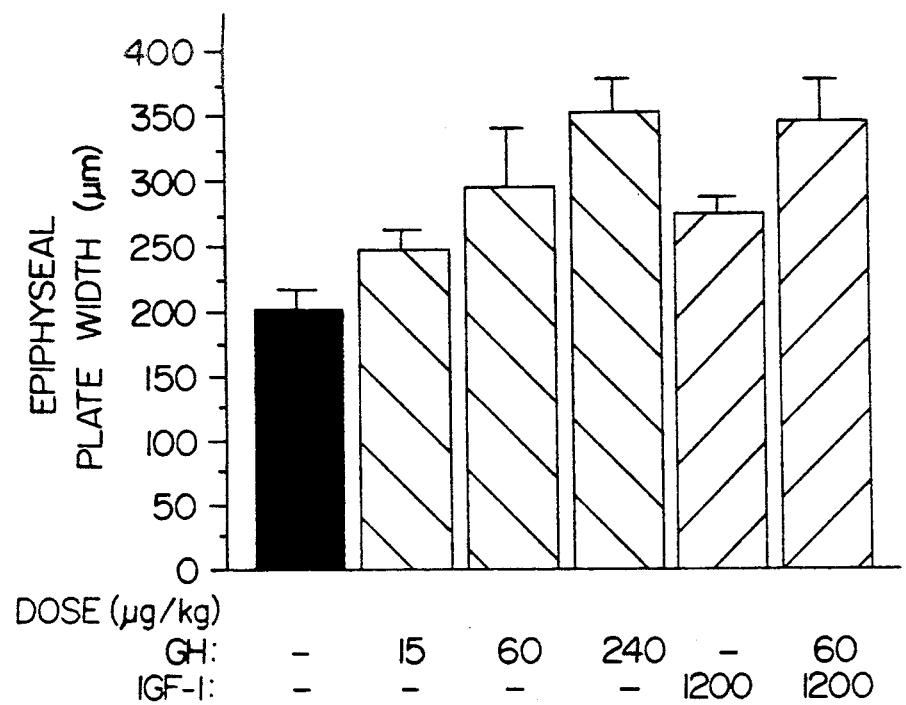
FIG. 2 shows a bar graph of the increase in width of epiphyseal bone growth plate after seven days of hGH and/or IGF-I treatment of hypophysectomized rats (means±SD).

FIG. 2 illustrates a bar graph of the increase in width of the epiphyseal bone growth plate after seven days of hGH and/or IGF-I treatment in hypophysectomized rats. The mean±SD for 7-9 rats per group is illustrated for Study 1. Statistically significant differences were assumed if $p<0.05$.

Figure 3A:
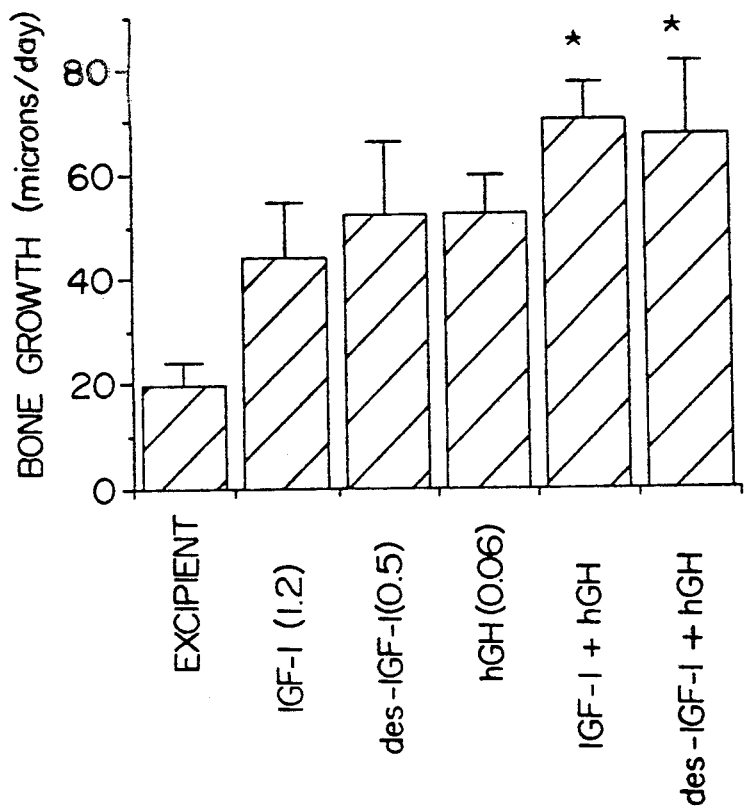
FIGS. 3A and 3B represent graphs of longitudinal bone growth and epiphyseal plate width (a separate study from FIG. 2), respectively, for each group of hypophysectomized rats treated with hGH alone, or IGF-I or des(1-3)-IGF-I alone or in combination with hGH (means±SD).
Figure 3B:
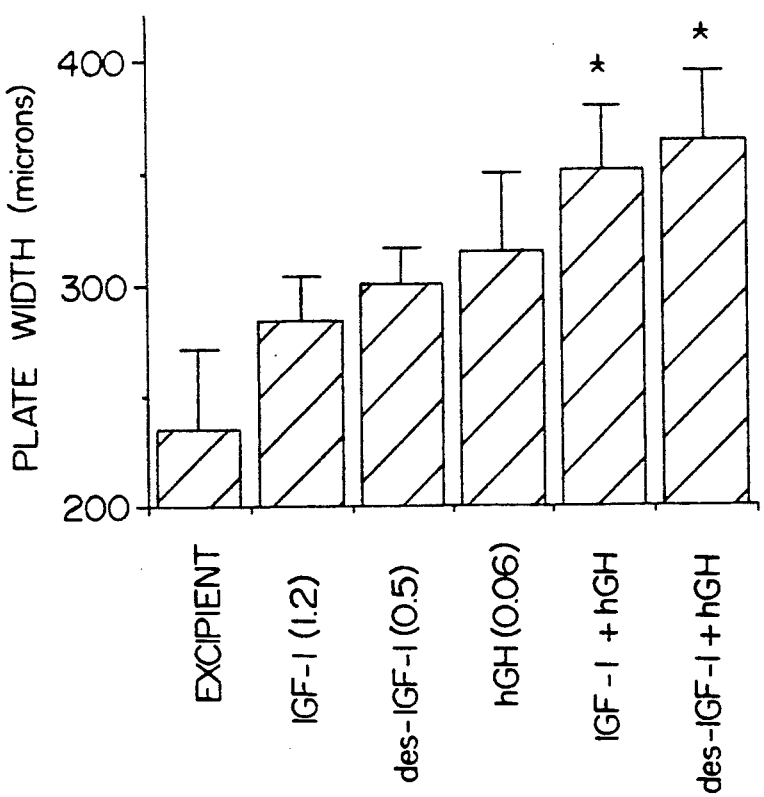

In Study 2, shown in FIG. 3B, the groups treated with 60 μg/kg/day of GH ($315\pm35$ μm) or with 120 μg/rat of IGF-I ($284\pm20$ μm) were significantly different ($t=6.859$, $p<0.001$; $t=4.00$, $p<0.01$, respectively) from the excipient group ($235\pm36$ μm); the plate width for GH plus IGF-I group ($35\pm29$ μm) differed from both the GH alone ($t=3.069$, $p<0.05$) and IGF-I alone ($t=5.535$, $P<0.001$). Thus, in both studies GH and IGF-I alone induced a significant widening of the tibial epiphysis as compared to the control group, whereas co-treatment with both hormones produced a greater width than treatment with either GH or IGF-I by itself, except at the high-dose GH level. In addition (FIG. 3B), des(1-3)-IGF-I also stimulated growth plate width to $300 \pm 17$ μm compared to excipient ($t = 5.545$, $p < 0.001$), and once again co-administration of GH resulted in a further increase in plate width to $364 \pm 31$ μm, which was greater than for des(1-3)-IGF-I alone ($t = 5.507$, $p < 0.001$) and GH alone ($t = 4.193$, $p < 0.01$). The epiphyseal cartilage widening in response to these hormone treatments was similar in pattern to the body weight changes (FIG. 1).

As with body weight gain, other investigators have tested the effects of such combination treatments on tibial bone growth. GH and IGF-I, delivered intravenously to rats by Skottner et al., *J. Endocrin.*, supra, induced no significantly greater response on tibial bone growth or epiphyseal cartilage width than that resulting from treatment with either hormone alone. The IGF-I did induce widening of the epiphyseal cartilage and lengthening of the bone, while having no effect on body weight, as noted above. In another experiment, direct administration of either of these hormones to the tibial epiphysis stimulated longitudinal bone growth. Isgaard et al., supra. However, the combination of IGF-I and GH yielded no greater growth than that achieved with GH alone.

FIG. 3 illustrates two measures of bone growth, longitudinal bone growth (FIG. 3A) and epiphyseal plate width (FIG. 3B, Study 2 as opposed to Study 1 shown in FIG. 2, where only epiphyseal plate width is shown), obtained in hypophysectomized rats treated for 7 days with IGF-I or des(1-3)-IGF-I alone or in combination with hGH. For both full-length IGF-I and des(1-3)-IGF-I, the results show that their combination with hGH yielded bone growth or cartilage expansion that was greater than the effect using either hormone alone and was additive.

The relevant changes in the weights of the five organs measured are as follows (Table 1). While GH inconsistently increased heart, thymus, and spleen, IGF-I and the combination of IGF-I and GH clearly increased all organ weights relative to the excipient group. The preferential effect of IGF-I on kidney, spleen, and thymus has been shown by others. Guler et al., *Proc. Natl. Acad. Sci. USA*. 85: 4889–4893 (1988). A significantly greater effect of the combination treatment was measured only in Study 2, for all organs except the thymus. Correcting for the body weight increment, the organ-to-body weight ratios were increased by IGF-I for kidneys, spleen, and thymus; the hormone combination did not amplify this effect in these three responsive tissues. In contrast, GH treatment did not alter the organ-to-body weight ratios.

These data indicate that at least a fraction of the hormone combination response can be attributed to weight increases in

TABLE 1

| GH AND IGF-I ELICIT DIFFERENT ORGAN WEIGHT RESPONSES | | | | |
|---|---|---|---|---|
| | Excipient | GH 60 ug/kg | IGF-I 1.2 mg/kg | GH + IGF-I |
| A. Absolute Wet Weights | | | | |
| *Study 1* | | | | |
| Heart (mg) | $291 \pm 20$ | $324 \pm 13\#$ | $341 \pm 24\#$ | $344 \pm 16\#$ |
| Kidneys (mg) | $650 \pm 46$ | $686 \pm 60^{ab}$ | $849 \pm 50\#^a$ | $869 \pm 31\#^b$ |
| Liver (g) | $3.80 \pm 0.17$ | $4.00 \pm 0.23^{ab}$ | $4.43 \pm 0.27\#^a$ | $4.44 \pm 0.39\#^b$ |
| Spleen (mg) | $234 \pm 56$ | $244 \pm 26^{ab}$ | $369 \pm 50\#^a$ | $389 \pm 54\#^b$ |
| Thymus (mg) | $233 \pm 24$ | $317 \pm 82\#^a$ | $391 \pm 49\#$ | $414 \pm 110\#^a$ |
| *Study 2* | | | | |
| Heart (mg) | $355 \pm 22$ | $374 \pm 43^a$ | $376 \pm 24^b$ | $440 \pm 65\#^{ab}$ |
| Kidneys (mg) | $688 \pm 37$ | $736 \pm 44^{ab}$ | $871 \pm 62\#^{ab}$ | $973 \pm 45\#^{bc}$ |
| Liver (g) | $3.77 \pm 0.25$ | $4.04 \pm 0.30^a$ | $4.42 \pm 0.41\#$ | $4.58 \pm 0.13\#^a$ |
| Spleen (mg) | $197 \pm 16$ | $260 \pm 24\#^a$ | $297 \pm 30\#^b$ | $342 \pm 23\#^{ab}$ |
| Thymus (mg) | $257 \pm 42$ | $336 \pm 50$ | $436 \pm 154\#$ | $450 \pm 113\#$ |
| B. Organ to Body Weight (BW) Ratio ($\times 10^{-3}$) | | | | |
| *Study 1* | | | | |
| Heart/BW | $3.00 \pm 0.19$ | $3.08 \pm 0.17$ | $3.10 \pm 0.21$ | $2.95 \pm 0.15$ |
| Kidneys/BW | $6.71 \pm 0.52$ | $6.51 \pm 0.57^{ab}$ | $7.70 \pm 0.38\#^a$ | $7.45 \pm 0.38\#^b$ |
| Liver/BW | $39.2 \pm 1.8$ | $37.9 \pm 1.7$ | $40.2 \pm 2.1$ | $38.0 \pm 2.2$ |
| Spleen/BW | $2.42 \pm 0.65$ | $2.31 \pm 0.27^{ab}$ | $3.35 \pm 0.47\#^a$ | $3.33 \pm 0.42\#^b$ |
| Thymus/BW | $2.41 \pm 0.28$ | $3.00 \pm 0.72$ | $3.55 \pm 0.97\#$ | $3.55 \pm 0.97\#$ |
| *Study 2* | | | | |
| Heart/BW | $3.91 \pm 0.22$ | $3.72 \pm 0.34$ | $3.69 \pm 0.25$ | $3.98 \pm 0.51$ |
| Kidneys/BW | $7.57 \pm 0.27$ | $7.33 \pm 0.30^{ab}$ | $8.56 \pm 0.64\#^a$ | $8.80 \pm 0.37\#^b$ |
| Liver/BW | $41.4 \pm 2.2$ | $40.2 \pm 1.9$ | $43.4 \pm 4.2$ | $41.4 \pm 1.0$ |
| Spleen/BW | $2.16 \pm 0.13$ | $2.69 \pm 0.52\#^a$ | $2.92 \pm 0.28^a$ | $3.09 \pm 0.21\#^a$ |
| Thymus/BW | $2.83 \pm 0.43$ | $3.35 \pm 0.48$ | $4.28 \pm 1.48\#$ | $4.06 \pm 0.99\#$ |

Mean ± SD (7–9 rats/group); the # denotes statistically different from excipient and similar letter superscripts denote group differences by Duncan's test after analysis of variance (ANOVA) at $p < 0.05$ In addition, they indicate that the additive effect of IGF-I and GH was not seen on all tissues, for example, for the absolute weight of thymus (Table 1), or for all the organ/body weight ratios. This varying sensitivity of different tissues to the combination of GH and IGF-I was unexpected. In some tissues, notably in whole body growth and on bone and cartilage, IGF-I and GH are both effective and additive. In other tissues, i.e., thymus, IGF-I and GH are both effective but not additive, indicating a selective effect.

EXAMPLE II

A. Combination Studies

In the two experiments described below, hypophysectomized rats as described in Example I (Study 3) or female dwarf rats (60–70 days of age, 100–140 g, Study 4) were anesthetized with ketamine/xylazine. Then 2 (for the dwarf rats) or 2 (for the hypophysectomized rats) osmotic minipumps (Alza 2001, delivery rate 1μl/hour/pump) were placed subcutaneously. The pumps contained either the excipient (10 mM citrate buffer and 126 mM NaCl, pH 6) or IGF-I (5 mg/ml) so that the approximate dose administered was 240 μg/rat/day (2.4 mg/kg assuming a 100 g rat) for both types of rats. The hGH formulation employed was that described in Example I. The IGF-I was prepared by direct secretion of the IGF-I gene from *E. coli* as in accordance with EP 128,733 published Dec. 19, 1984 or EP 288,451 published Oct. 26, 1988, and expected to have a specific activity of >about 14,000 U/mg by radioreceptor assay using placental membranes, or was obtained from KabiGen AB (specific activity >14,000 U/mg) or from Genentech, Inc. as described in Example I. It was formulated as described in Example I. In Study 3 the solubility of hGH was increased by adding 0.1% Tween 20 to the 5 mM phosphate buffer (pH 7.8). The hGH in both studies was given daily as a single 0.1-ml subcutaneous injection.

In Study 3 (hypophysectomized rats) the experimental groups were:
1) Excipient pump, excipient injections
2) IGF-I pump (2.4 mg/kg), excipient injections
3) Excipient pump, hGH injections (50.0 mg/kg)
4) Excipient pump, hGH injections (10.0 mg/kg)
5) Excipient pump, hGH injections (2 mg/kg)
6) Excipient pump, hGH injections (0.4 mg/kg)
7) Excipient pump, hGH injections (0.08 mg/kg)
8) IGF-I pump (2.4 mg/kg), hGH injections (50.0 mg/kg)
9) IGF-I pump (2.4 mg/kg), hGH injections (10.0 mg/kg)
10) IGF-I pump (2.4 mg/kg), hGH injections (2.0 mg/kg)
11) IGF-I pump (2.4 mg/kg), hGH injections (0.4 mg/kg)
12) IGF-I pump (2.4 mg/kg), hGH injections (0.08 mg/kg).

In Study 4 (dwarf rats) the experimental groups were:
1) Excipient pump, excipient injections
2) IGF-I pump (2.4 mg/kg), excipient injections
3) Excipient pump, hGH injections (2.0 mg/kg)
4) Excipient pump, hGH injections (0.5 mg/kg)
5) Excipient pump, hGH injections (0.125 mg/kg)
6) IGF-I pump (2.4 mg/kg), hGH injections (2.0 mg/kg)
7) IGF-I pump (2.4 mg/kg), hGH injections (0.5 mg/kg)
8) IGF-I pump (2.4 mg/kg), hGH injections (0.125 mg/kg).

Figure 4:
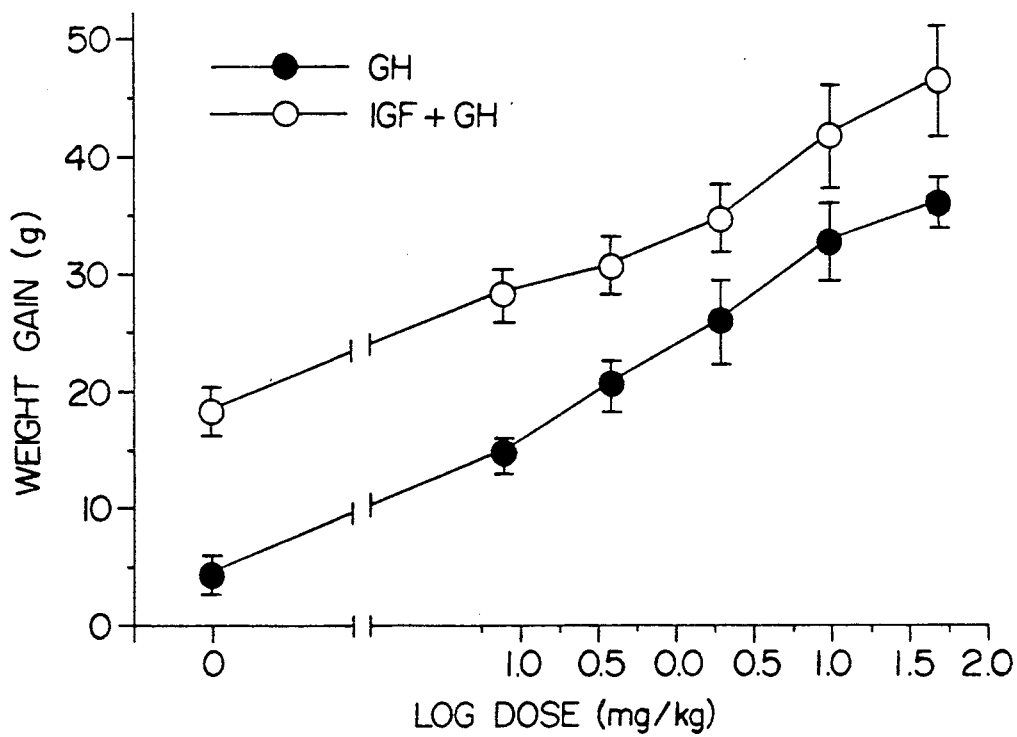
FIG. 4 illustrates a graph of weight gain in hypophysectomized rats over one week as a function of hGH concentration (log dose), where rats were treated with IGF-I (2.4 mg/kg/day) using minipumps and with hGH daily injections (means±SD).

FIG. 4 shows the results from Study 3 for the 7-day weight gains in the hypophysectomized rat. The excipient gave a weight gain of $4.46 \pm 1.66$ g and IGF-I at 240 μg/day gave a weight gain of $18.23 \pm 1.98$ g. Once more, the inclusion of IGF-I in the minipumps greatly enhanced the potency of daily injections of hGH in promoting weight gain. The weight gain responses to hGH or hGH plus IGF-I were analyzed as a parallel line bioassay against log dose of hGH. The two dose response lines fulfilled the criteria for a bioassay, as they were statistically proved to be linear and parallel. The potency of hGH plus IGF-I was 26.6 times that of hGH alone (95% confidence, 14.8 to 5.71), with the difference between the two dose-response lines being highly significant (1,49 degrees of freedom (d.f.), $F=169.4$, $p<0.0001$).

Figure 5:
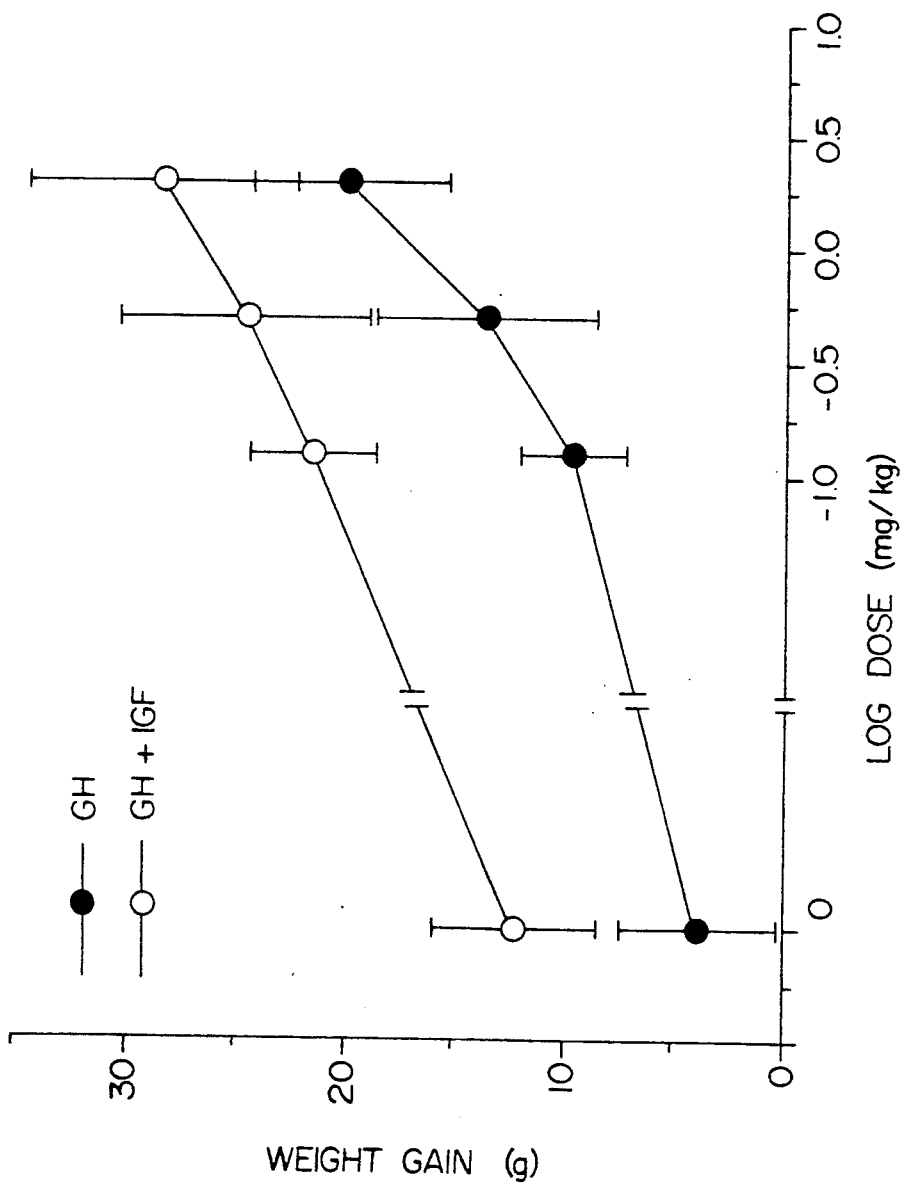
FIG. 5 illustrates a graph of weight gain in dwarf rats over one week as a function of hGH concentration (log dose), where rats were treated with IGF-I (1.2 mg/kg/day) using minipumps and with hGH daily injections (means±SD).

FIG. 5 shows the weight gains over 7 days from Study 4. The excipient gave a weight gain of $3.95 \pm 3.56$ g and IGF-I at 240 μg/day gave a weight gain of $12.15 \pm 3.76$ g. The weight gain responses to hGH or hGH plus IGF-I were analyzed as a parallel line bioassay against log dose of hGH. The two dose response lines fulfilled the criteria for a bioassay, as they were statistically proved to be linear and parallel. Individually, IGF-I and hGH gave substantial weight gains in the dwarf rat. The relative potency of the hGH plus IGF-I was 28.9 times that of the hGH alone (95% confidence limits, 7.7 to 514.6), with the difference between the two dose-response lines being highly significant (1,30 d.f., $F=45.75$, $p<0.0001$).

B. Dose Response Curve of IGF-I Alone

Figure 6:
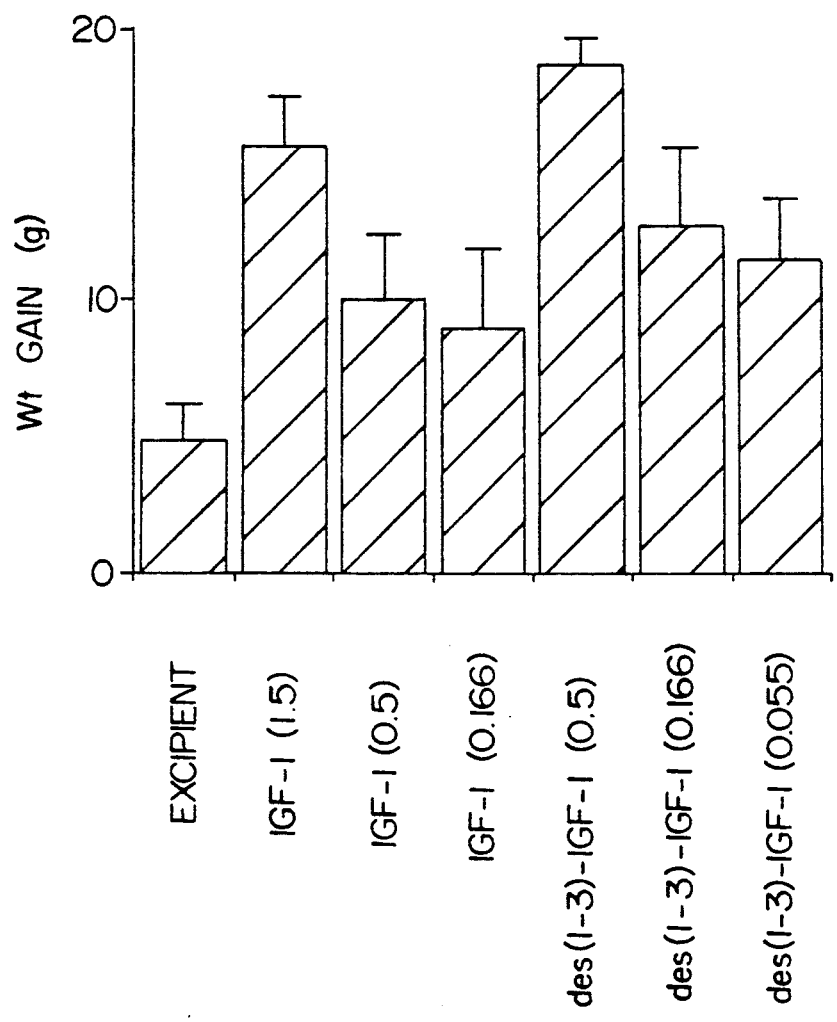
FIG. 6 depicts a graph of weight gain in hypophysectomized rats using three different doses of IGF-I or des(1-3)-IGF-I infused subcutaneously by minipumps for seven days (means±SD).

FIG. 6 illustrates the weight gain of hypophysectomized rats treated with excipient (citrate buffer as described above), or the IGF-I or des(1-3)-IGF-I used in Example I at three different doses subcutaneously using minipumps for seven days, following the general protocol described in Example I. This figure illustrates the minimal doses of IGF-I and des(1-3)-IGF-I for bioactivity in the rat.

C. Dose Response Curve of hGH Alone

Figure 7:
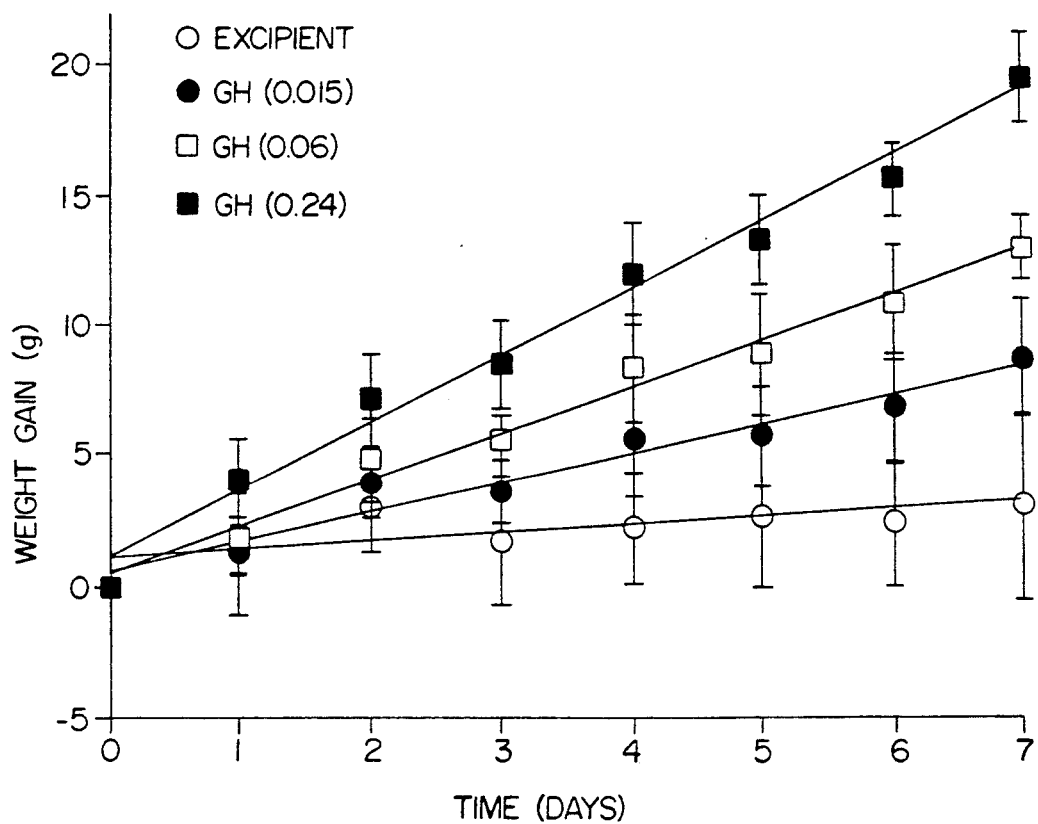
FIG. 7 depicts a graph of weight gain in hypophysectomized rats using three different doses of hGH injected daily subcutaneously for seven days (means±SD).

FIG. 7 illustrates the weight gains of hypophysectomized rats treated with excipient or three different doses of the hGH of Examples I and II daily subcutaneously for seven days, following the general protocol described in Example I. This figure illustrates the minimal doses of GH for bioactivity in the rat. At day 7, low-dose GH showed a greater weight gain than excipient ($2.9 \pm 3.5$ g vs. $8.6 \pm 2.3$ g, $t=7.03$, $p<0.001$), which was in turn less than medium-dose GH ($12.9 \pm 1.2$ g, $t=4.91$, $p<0.01$).

In the two animal models of GH deficiency (Studies 3 and 4), the potency of hGH administered as a daily subcutaneous injection was increased over 25 fold by co-treatment with IGF-I. This result in the hypophysectomized rat might be explained by the relative lack of hormones (thyroid and glucocorticoids) known to be permissive for hGH action leading to a poor IGF-I generation. However, the result in the dwarf rat, where only hGH appears to be lacking, with all the other hormone systems (especially the thyroid and adrenal hormones) being normal, indicates that the additive effect of hGH and IGF-I occurs independent of the status of thyroid or adrenal hormones. However, the close agreement in the two models of the enhanced potency of hGH due to IGF-I and the magnitude of the effect (about 25X) is surprising.

The doses of hGH that were used in Study 3 have rarely been used in the hypophysectomized rat, and the literature is unclear as to the dose of hGH that gives a maximal growth response. Doses of 10 and 50 mg/kg/day given as single daily subcutaneous injections for one week produce a maximal growth response. But the dose responses for the two regimes (hGH and hGH plus IGF-I) were parallel, even over this 625-fold dose range of five doses of hGH, including the two maximal doses of hGH. Therefore, the maximal growth response to hGH can clearly be increased if IGF-I is co-administered. This is surprising, as the maximal weight gain response to IGF-I in the hypophysectomized rat appears to be less than the weight gain in response to hGH.

The range of doses of hGH over which IGF-I would be predicted to have an additive effect on weight gain is clearly the full range of effective GH dose, in the hypophysectomized rat from 0.01 to 50 mg/kg. In the dwarf rat the maximal effective doses of hGH are not known, but 50 mg/kg would also be assumed to be an effective maximal dose of hGH. The previous work in the hypophysectomized rat has shown 2.4 mg/kg of IGF-I delivered as a subcutaneous infusion for one week to be near to maximal, as higher doses of IGF-I cause fatal hypoglycemia. The minimal effective dose of IGF-I in the hypophysectomized rat is around 0.1 mg/kg per day.

In the dwarf rat, 2.4 mg/kg of IGF-I was used, while in the hypophysectomized rat both 1.2 mg/kg and 2.4 mg/kg doses of IGF-I were used (Examples I and II), yet an additive effect of IGF-I and GH was observed despite different doses of IGF-I being used. The full dose response curves for GH alone and GH plus IGF-I were parallel, which implies that at any dose of hGH, even at a very small dose of hGH that by itself might not give a measurable response, the effects of IGF-I and GH would be additive. It would therefore be expected that at any daily dose of GH (from 0.01 to 50 mg/kg) or IGF-I (from 0.1 to 2.4 mg/kg) the two molecules would have additive effects on body growth.

EXAMPLE III

Two Clinical Scenarios for the Combination Treatment

Two examples of pertinent clinical scenarios are described below that will undoubtedly benefit from concomitant administration of GH and IGF-I.

1. Patients who exhibit a slowing in growth rate after at least twelve months of GH administration.

Figure 8B:
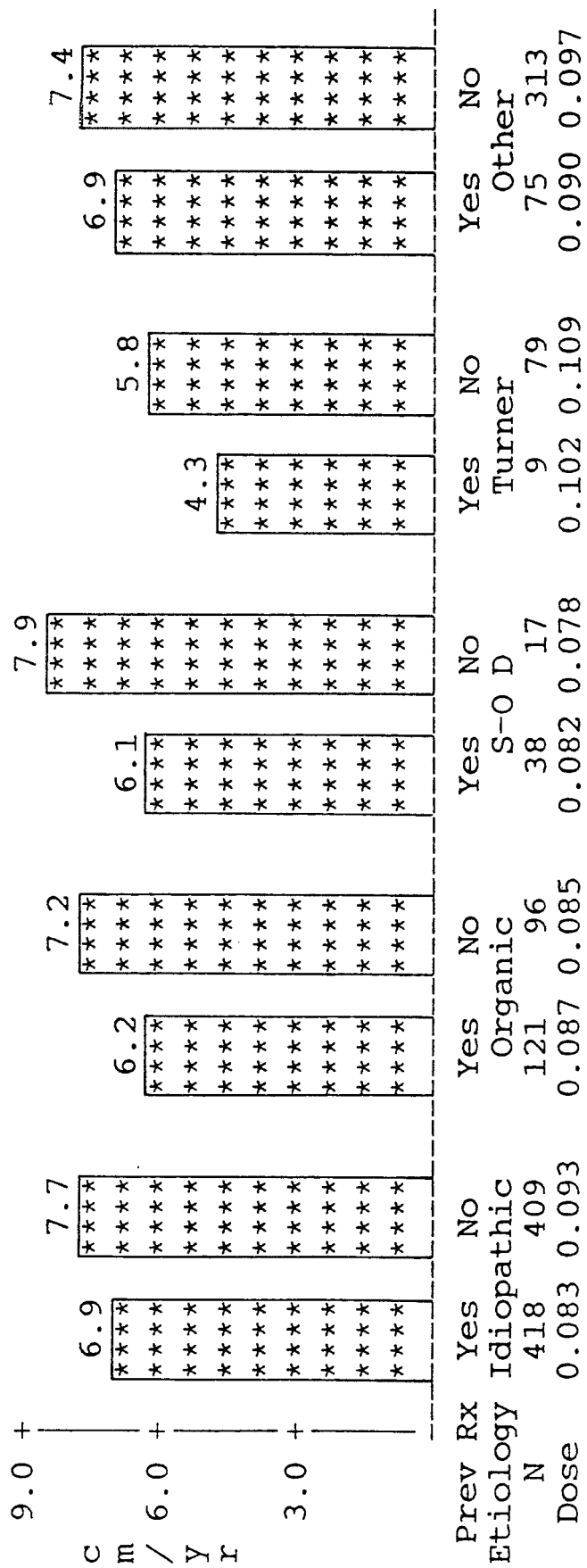

It is well recognized by pediatric endocrinologists that either naive (no previous treatment) or previously treated patients (following a break in GH administration) exhibit a second-year fall in growth rate. This phenomenon is independent of the etiology of the type of short stature or GH deficiency (e.g., whether idiopathic, organic, septo-optic dysplasia (S-O D), Turner, or other). See FIG. 8.

Thus, during the period where the growth rate is slowing, IGF-I treatment together with GH treatment would increase the annualized rate to compensate for this second-year loss in response.

2. Patients who have little time for GH administration to be maximally effective.

Figure 9:
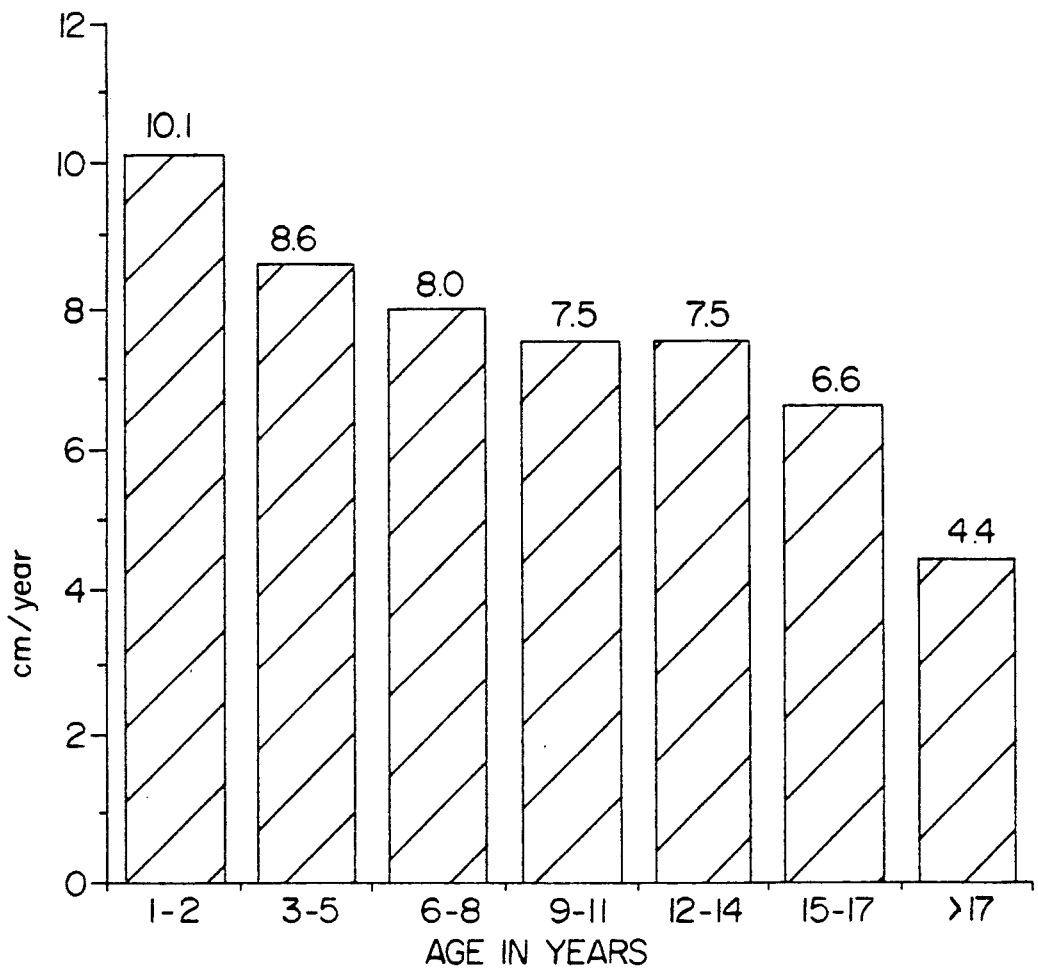
FIG. 9 illustrates bar graphs of the annualized (12-month) growth rate in cm/year of patients treated with the indicated dose of hGH in the 1-2, 3-5, 6-8, 9-11, 12-4, 15-17, and more than 17 year ranges. N indicates the number of patients in each age group.

If patients are older when they are diagnosed with GH deficiency, less time is available to correct their resultant short stature. This is illustrated in FIG. 9, where the annualized growth rate is reported for patients in seven age groups. Older patients have only, for example, 2-3 years left before their growth plates close, making further linear growth unlikely. These patients could be treated with the combination of IGF-I and hGH to allow optimization of their growth rates.

DISCUSSION AND SUMMARY

The results shown herein have significance in medicine and agriculture in any situation where GH or IGF-I treatment is used. This regime of combined IGF-I and GH treatment would allow smaller doses of GH (approximately 25-fold less) to be given to produce equivalent responses to treatment with GH alone. This would be of particular importance in situations where the side effects of GH treatment (i.e., hyperinsulinemia, hyperglycemia) should be minimized. In diabetes, combined GH and IGF-I treatment, with smaller GH doses being possible, would minimize the insulin-resistant effect of the administered GH. In patients where the anabolic effect of GH is reduced, possibly by a reduced ability to produce an IGF-I response to the administered GH, co-treatment with GH and IGF-I would also be expected to give a larger anabolic response.

A broad class of patients where the regime of combined GH and IGF-I treatment would be beneficial is in adult patients where the IGF-I response to GH is naturally reduced. In adults, the unwanted effects of GH (insulin resistance) may be a direct consequence of a reduced IGF-I response to administered GH. In adults, the co-administration of GH and IGF-I might be viewed as restoring the situation in a younger animal where there is a more vigorous IGF-I response to GH treatment.

The mode of administration of the GH in the present studies was intermittent, by daily subcutaneous injection. However, at the largest doses used (50 mg/kg), considerable concentrations of hGH would have persisted in the blood at physiologically effective concentrations, making the blood concentrations of hGH always at a level that would provide a stimulus to GH receptors. Therefore, at the highest dose the tissue exposure to hGH was in essence one of continuous exposure, so that the growth response to administering hGH as a continuous infusion would likely be enhanced by the co-administration of IGF-I. The potency of hGH delivered in any manner that would stimulate body growth or be anabolic would be expected to increase if IGF-I were co-administered. Also, it is likely that the improved potency of co-administered hGH and IGF-I would allow less frequent injections of hGH or IGF-I than for hGH alone.

IGF-I was delivered as a continuous infusion, because previous studies showed that IGF-I given alone as injections is less effective at enhancing body growth. However, the combination of GH plus IGF-I would allow the use of sub-optimal regimes of IGF-I administration, such as injections, when combined with GH treatment.

In conclusion, cotreatment of hypophysectomized or dwarf rats with GH and IGF-I or des(1-3)-IGF-I amplifies the body weight gain, longitudinal bone growth, and tibial epiphyseal widening relative to the response to either hormone alone. This finding indicates for the first time that exogenous IGF-I can increase some growth responses initiated by GH in a manner that is at least additive. Thus, the IGF-I is effective at increasing the responses to GH treatment or at decreasing the amount of GH needed to produce a significant response.

What is claimed is:

1. A method for enhancing growth of a mammal comprising administering systemically and concurrently to the mammal effective amounts of IGF-I and GH, wherein the GH is administered by injections, so as to enhance said growth of the mammal over the enhancement in growth achieved using an equivalent dose of IGF-I or GH alone, without incurring hypoglycemia.

2. The method of claim 1 wherein the mammal is an animal.

3. The method of claim 2 wherein the GH and IGF-I are bovine, ovine, or porcine GH or IGF-I, and the animal is bovine, ovine, or porcine, respectively.

4. The method of claim 1 wherein the mammal is a human.

5. The method of claim 4 wherein the human is a non-adult.

6. The method of claim 4 wherein the IGF-I is human native-sequence, mature IGF-I and the GH is human native-sequence, mature GH.

7. The method of claim 6 wherein the IGF-I has no N-terminal methionine.

8. The method of claim 6 wherein the IGF-I has a specific activity of greater than about 14,000 units/mg by radioreceptor assay using placenta membranes.

9. The method of claim 6 wherein the IGF-I is a human native-sequence IGF-I analog having the glutamic acid at position 3 replaced by another amino acid or deleted.

10. The method of claim 9 wherein the IGF-I is des(-1-3)-IGF-I.

11. The method of claim 10 wherein the des(1-3)-IGF-I is in a sterile, isotonic solution containing acetic acid, pH 3.2 to 4.5.

12. The method of claim 6 wherein the IGF-I is in a sterile, isotonic solution containing a citrate buffer, pH 6.

13. The method of claim 6 wherein the GH is recombinant GH.

14. The method of claim 13 wherein the GH is in a sterile, isotonic solution containing mannitol and a phosphate buffer, pH 7.4-7.8.

15. The method of claim 1 wherein the IGF-I is administered by continuous infusion.

16. The method of claim 15 wherein the administration of GH or IGF-I or both is by the subcutaneous or intravenous route.

17. The method of claim 1 wherein the administration of both GH and IGF-I is by the subcutaneous route.

18. The method of claim 15 wherein the GH is injected once daily.

19. The method of claim 1 wherein the effective amount of each of GH and IGF-I is at least 0.1 mg/kg/day.

20. The method of claim 4 wherein the effective amount of each of GH and IGF-I is at least 1 mg/kg/day.

21. The method of claim 1 wherein the IGF-I and GH are administered separately.

22. The method of claim 1 wherein the IGF-I and GH are administered as a single formulation.

23. The method of claim 4 wherein the human to be treated has diabetes.

24. The method of claim 4 wherein the human to be treated experiences hyperinsulinemia or hyperglycemia with GH treatment alone.

25. The method of claim 4 wherein the human to be treated exhibits a reduced anabolic effect when treated with GH alone.

26. The method of claim 25 wherein the human to be treated has reached a maximum growth level and then a decrease in annualized growth rate after having previously been treated with GH alone.

27. The method of claim 25 wherein the human to be treated is at an age that is 2-3 years before his or her growth plate closes.

28. The method of claim 4 wherein the effective amount of GH is less than the dose that gives a maximal growth response using GH alone.

29. The method of claim 4 wherein the effective amount of GH is greater than the dose that gives a maximal growth response using GH alone.

* * * * *